United States Patent
Arimoto

(10) Patent No.: US 11,977,018 B2
(45) Date of Patent: May 7, 2024

(54) DETECTION METHOD AND DETECTION DEVICE

(71) Applicant: Panasonic Intellectual Property Management Co., Ltd., Osaka (JP)

(72) Inventor: Satoshi Arimoto, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 333 days.

(21) Appl. No.: 17/491,585

(22) Filed: Oct. 1, 2021

(65) Prior Publication Data

US 2022/0018753 A1    Jan. 20, 2022

Related U.S. Application Data

(63) Continuation of application No. PCT/JP2020/020654, filed on May 26, 2020.

(30) Foreign Application Priority Data

Jun. 20, 2019  (JP) ................................. 2019-114499

(51) Int. Cl.
    G01N 15/1031    (2024.01)
    G01N 15/1429    (2024.01)
    G01N 15/1434    (2024.01)

(52) U.S. Cl.
    CPC ..... *G01N 15/1031* (2013.01); *G01N 15/1429* (2013.01); *G01N 2015/144* (2013.01)

(58) Field of Classification Search
    CPC ........... G01N 15/1031; G01N 15/1429; G01N 2015/144; G01N 15/1425; G01N 15/1463;
    (Continued)

(56) References Cited

U.S. PATENT DOCUMENTS

| | | | | | |
|---|---|---|---|---|---|
| 4,634,669 A | * | 1/1987 | Arnold | ................... | G01N 15/00 435/207 |
| 4,801,543 A | * | 1/1989 | Arnold | ................... | G01N 15/00 436/151 |

(Continued)

FOREIGN PATENT DOCUMENTS

| | | |
|---|---|---|
| JP | 2000-508574 | 7/2000 |
| JP | 2011-196859 | 10/2011 |

(Continued)

OTHER PUBLICATIONS

Huang, Ying, et al. "Differences in the AC electrodynamics of viable and non-viable yeast cells determined through combined dielectrophoresis and electrorotation studies." Physics in Medicine & Biology 37.7 (1992): 1499. (Year: 1992).*

(Continued)

*Primary Examiner* — Christopher P McAndrew
(74) *Attorney, Agent, or Firm* — Wenderoth, Lind & Ponack, L.L.P.

(57) ABSTRACT

A target substance detection method includes forming a complex by causing a target substance and a dielectric particle to bind to each other, the dielectric particle being modified with a substance (for example, an antibody) having a property of specifically binding to the target substance; subjecting a bound particle and an unbound particle to dielectrophoresis in a liquid, the bound particle being the dielectric particle constituting the complex, the unbound particle being a dielectric particle not constituting the complex; and detecting the target substance in the complex, based on a difference in motion between the bound particle and the unbound particle caused by the dielectrophoresis.

5 Claims, 8 Drawing Sheets

(58) Field of Classification Search
CPC ... G01N 2001/4038; G01N 2015/0693; G01N 2015/1006; G01N 21/64; G01N 27/00; G01N 33/483; G01N 33/543; G01N 27/447; B03C 5/005; B03C 5/026; B03C 2201/18; B03C 2201/26
USPC ........................................................ 324/71.1
See application file for complete search history.

(56) References Cited

U.S. PATENT DOCUMENTS

| | | | |
|---|---|---|---|
| 8,277,753 B2 * | 10/2012 | Hasan | ................... B01L 3/0244 422/50 |
| 2002/0190732 A1 | 12/2002 | Cheng et al. | |
| 2019/0154580 A1 | 5/2019 | Yasuura et al. | |

FOREIGN PATENT DOCUMENTS

| | | |
|---|---|---|
| JP | 2015-109826 | 6/2015 |
| WO | 1997/034689 | 9/1997 |
| WO | 2017/187744 | 11/2017 |

OTHER PUBLICATIONS

Morganti, Diego. AC electrokinetic analysis of chemically modified microparticles. Diss. University of Southampton, 2012. (Year: 2012).*
Goater, A. D., and R. Pethig. "Electrorotation and dielectrophoresis." Parasitology 117.7 (1999): 177-189. (Year: 1999).*
International Search Report of PCT application No. PCT/JP2020/020654 dated Aug. 11, 2020.
Kosuke Ino et al., "Electrorotation chip consisting of three-dimensional interdigitated array electrodes", Sensors and Actuators B 153 (2011), Nov. 16, 2010, 468-473.

* cited by examiner

DETECTION METHOD AND DETECTION DEVICE

BACKGROUND

1. Technical Field

The present disclosure relates to a detection method and a detection device for detecting a target substance such as a virus.

2. Description of the Related Art

In the related art, there is provided an optical detection method for highly sensitively detecting a minute target substance by using a near field. For example, in International Publication No. 2017/187744, a target substance is detected by measuring, for example, a decrease caused in an optical signal in response to application of a first magnetic field that causes a bound body, which is formed as a result of the target substance binding to a magnetic particle and a fluorescent particle, to move in a direction away from a surface of a detection plate where a near field is formed.

SUMMARY

However, in International Publication No. 2017/187744, a bound body formed by non-specific adsorption in which a magnetic particle and a fluorescent particle bind to each other without any target substance also moves while emitting fluorescence. Thus, it is difficult to distinguish this bound body from a bound body including the target substance. As a result, false positives in which the target substance is falsely detected because of the bound body not including the target substance may occur, and detection accuracy may decrease.

One non-limiting and exemplary embodiment provides a target substance detection technique capable of reducing false positives caused by non-specific adsorption and improving target substance detection accuracy.

In one general aspect, the techniques disclosed here feature a detection method including forming a complex by causing a target substance and a dielectric particle to bind to each other, the dielectric particle being modified with a substance having a property of specifically binding to the target substance; subjecting a bound particle and an unbound particle to dielectrophoresis in a liquid, the bound particle being the dielectric particle constituting the complex, the unbound particle being a dielectric particle not constituting the complex; and detecting the target substance included in the complex, based on a difference in motion between the bound particle and the unbound particle caused by the dielectrophoresis.

According to the one non-limiting and exemplary embodiment, false positives caused by non-specific adsorption can be reduced and target substance detection accuracy can be improved.

It should be noted that general or specific embodiments may be implemented as a system, a device, a method, an integrated circuit, a computer program, a computer-readable recording medium, or any selective combination thereof. Examples of the computer-readable recording medium include a nonvolatile recording medium such as a compact disc read-only memory (CD-ROM).

Additional benefits and advantages of the disclosed embodiments will become apparent from the specification and drawings. The benefits and/or advantages may be individually obtained by the some embodiments and features of the specification and drawings, which need not all be provided in order to obtain one or more of such benefits and/or advantages.

DETAILED DESCRIPTION

Figure 1:
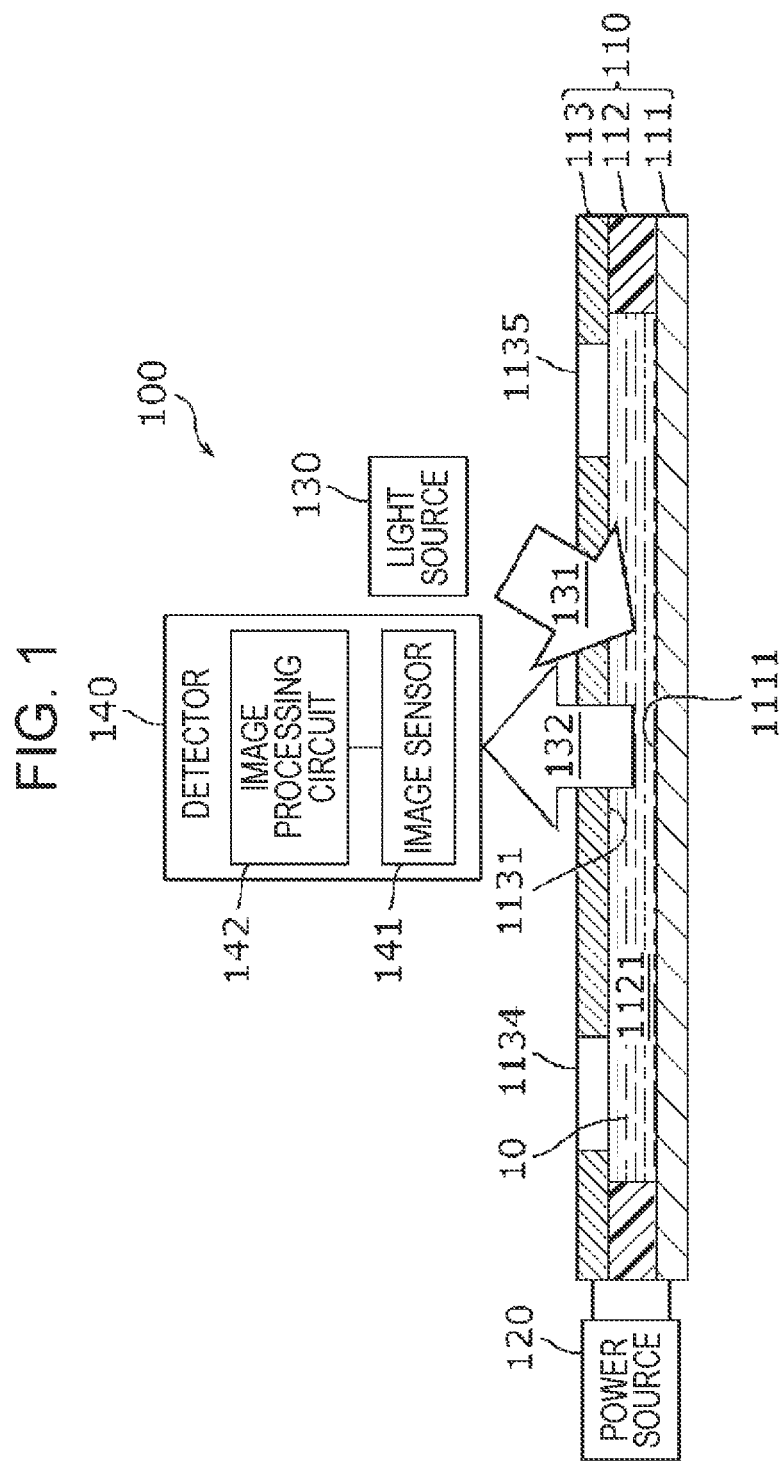
FIG. 1 is a diagram illustrating a configuration of a detection device according to an embodiment.

An embodiment will be specifically described below with reference to the accompanying drawings.

Note that the embodiment described below presents general or specific examples. The numerical values, shapes, materials, components, arranged positions and connections of the components, steps, the order of the steps, etc. described in the following embodiment are merely an example and are not intended to limit the claims. In addition, each drawing does not necessarily present a precise illustration. The same or substantially the same components are denoted by the same reference sign in the drawings, and duplicate description may be omitted or simplified.

Hereinafter, the terms describing relationships between the components, such as "parallel" and "perpendicular", the terms describing shapes of the components, such as "rectangular", and ranges of the numerical values are not used in a strict sense but are used to indicate substantially equivalent ranges with a tolerance of several %, for example.

In addition, hereinafter, detecting a target substance not only indicates finding the target substance to confirm the presence of the target substance but also measuring a quantity of the target substance (for example, the number or concentration) or a range of the quantity.

Embodiment

In an embodiment, a target substance included in complexes are detected based on a difference in motion between bound particles and unbound particles in a liquid in which an electric field that causes dielectrophoresis (DEP) is produced.

Dielectrophoresis is a phenomenon in which a force is exerted on a dielectric particle that is subjected to a non-uniform electric field. This force does not require the particle to be charged.

A target substance is a substance to be detected and refers to, for example, molecules of a pathogenic protein or the like, a virus (such as a capsid protein), or a bacterium (such as a polysaccharide). The target substance may also be referred to as a substance of interest or a detection target.

An embodiment of a detection device and a detection method that implement detection of a target substance by using dielectrophoresis will be specifically described below with reference to the accompanying drawings.

Configuration of Detection Device 100

A configuration of a detection device 100 will be described first with reference to FIG. 1. FIG. 1 is a diagram illustrating a configuration of the detection device 100 according to an embodiment. As illustrated in FIG. 1, the detection device 100 includes a dielectrophoresis device 110, a power source 120, a light source 130, and a detector 140.

The dielectrophoresis device 110 subjects bound particles and unbound particles to dielectrophoresis in a liquid. The bound particles are dielectric particles constituting complexes. The unbound particles are dielectric particles not constituting complexes. In this embodiment, the dielectrophoresis device 110 causes the bound particles and the unbound particles to move differently by dielectrophoresis. FIG. 1 illustrates a cross-section of the dielectrophoresis device 110.

A complex is a bound body of a target substance and a dielectric particle modified with a substance having a property of specifically binding to the target substance. That is, in the complex, the target substance and the dielectric particle bind to each other with the substance having the property of specifically binding to the target substance therebetween.

A dielectric particle is a particle that can be polarized by an electric field applied thereto. In this embodiment, the dielectric particle includes a fluorescent substance. Note that the dielectric particle may be a particle including a fluorescent substance or a particle not including any fluorescent substance. For example, a resin particle such as a polystyrene particle, a glass particle, or the like is used as the dielectric particle. The size of the dielectric particle is, for example, about 100 to 1000 nm.

A substance having a property of specifically binding to a target substance (hereinafter, referred to as a specifically binding substance) is a substance that can specifically bind to the target substance. Examples of the specifically binding substance for the target substance include an antibody for an antigen, an enzyme for a substrate or a coenzyme, a receptor for a hormone, protein A or G for an antibody, the avidin family for biotin, calmodulin for calcium, and lectins for sugar.

A bound particle is a dielectric particle constituting a complex, that is, a dielectric particle that has bound to the target substance with the specifically binding substance therebetween. The bound particle or the complex is also referred to as a bound component.

An unbound particle is a dielectric particle not constituting any complex, that is, a dielectric particle that has not bound to any target substance. The unbound particle is also referred to as a free component.

An internal configuration of the dielectrophoresis device 110 will now be described. As illustrated in FIG. 1, the dielectrophoresis device 110 includes a first substrate 111, a spacer 112, and a second substrate 113.

The first substrate 111 has a first electrode set 1111 to which alternating-current (AC) voltages are applied from the power source 120. For example, an indium tin oxide (ITO) glass substrate can be used as the first substrate 111. Details of the first electrode set 1111 will be described later with reference to FIG. 2.

The spacer 112 is a sheet-like member having a through hole and is disposed between the first substrate 111 and the second substrate 113. For example, a polyester film can be used as the spacer 112. The spacer 112 has a thickness of about 10 μm, for example. A channel 1121 is formed between the first substrate 111 and the second substrate 113 by the through hole of the spacer 112. A sample liquid 10 that can contain complexes and unbound particles is introduced to the channel 1121.

The second substrate 113 has a second electrode set 1131 to which AC voltages are applied from the power source 120. For example, an ITO glass substrate can be used as the second substrate 113. Details of the second electrode set 1131 will be described later with reference to FIG. 3.

The second substrate 113 has a supply hole 1134 and a discharge hole 1135 that are connected to the channel 1121. The sample liquid 10 is supplied to the channel 1121 through the supply hole 1134 and is discharged from the channel 1121 through the discharge hole 1135.

The power source 120 is an AC power source and applies AC voltages to the first electrode set 1111 of the first substrate 111 and the second electrode set 1131 of the second substrate 113. The power source 120 may be any power source capable of supplying AC voltages and is not limited to a power source of a specific kind. The AC voltages may be supplied from an external power source. In this case, the detection device 100 need not include the power source 120.

The light source 130 irradiates the sample liquid 10 in the channel 1121 with excitation light 131. Specifically, the dielectric particles in the sample liquid 10 are irradiated with the excitation light 131. In this embodiment, since the dielectric particles include the fluorescent substance, the fluorescent substance is excited by the excitation light 131 to emit fluorescence 132.

Any known technology can be used in the light source 130 without limitation. For example, a laser such as a semiconductor laser or a gas laser can be used as the light source 130. As a wavelength of the excitation light 131 emitted from the light source 130, a wavelength (for example, 400 nm to 2000 nm) that causes a small interaction with a substance included in a virus may be used. In addition, as the wavelength of the excitation light 131, a wavelength (for example, 600 nm to 850 nm) that can be used by a semiconductor laser may be used.

The detection device 100 need not include the light source 130. For example, when the dielectric particles are large enough to be recognizable in a two-dimensional image, the dielectric particles need not include the fluorescent substance. In this case, the dielectric particles need not be irradiated with excitation light.

The detector 140 detects the target substance included in the complexes based on a difference in motion between the bound particles and the unbound particles caused by dielectrophoresis. Specifically, the detector 140 includes an image sensor (imaging element) 141 and an image processing circuit 142.

The image sensor 141 is, for example, a charge-coupled device (CCD) image sensor or a complementary metal-oxide semiconductor (CMOS) image sensor. The image sensor 141 captures an image of the sample liquid 10 over time. Specifically, when the bound particles and the unbound particles are subjected to dielectrophoresis by the dielectrophoresis device 110, the image sensor 141 captures a moving image of the bound particles and the unbound particles in the sample liquid 10. In this embodiment, the image sensor 141 captures an image of the fluorescence emitted from the fluorescent substance included in the dielectric particles.

The image processing circuit 142 processes the moving image obtained from the image sensor 141 to distinguish between the motion of the bound particles and the motion of the unbound particles. The image processing circuit 142 detects the target substance included in the complexes based on the distinguished motion of the bound particles.

Note that the image processing circuit 142 may be implemented by a dedicated electronic circuit or by a processor and a memory that stores instructions. When the instructions are executed, the processor detects the target substance from the moving image.

The detection device 100 may include an optical lens, an optical filter, or an optical lens and an optical lens between the light source 130 and the dielectrophoresis device 110, between the dielectrophoresis device 110 and the image sensor 141, or between the light source 130 and the dielectrophoresis device 110 and between the dielectrophoresis device 110 and the image sensor 141. For example, a longpass filter that can block the excitation light 131 emitted from the light source 130 and allow the fluorescence 132 emitted by the fluorescent substance to pass therethrough may be disposed between the dielectrophoresis device 110 and the image sensor 141.

Shape and Arrangement of First Electrode Set 1111 on First Substrate 111

Figure 2:
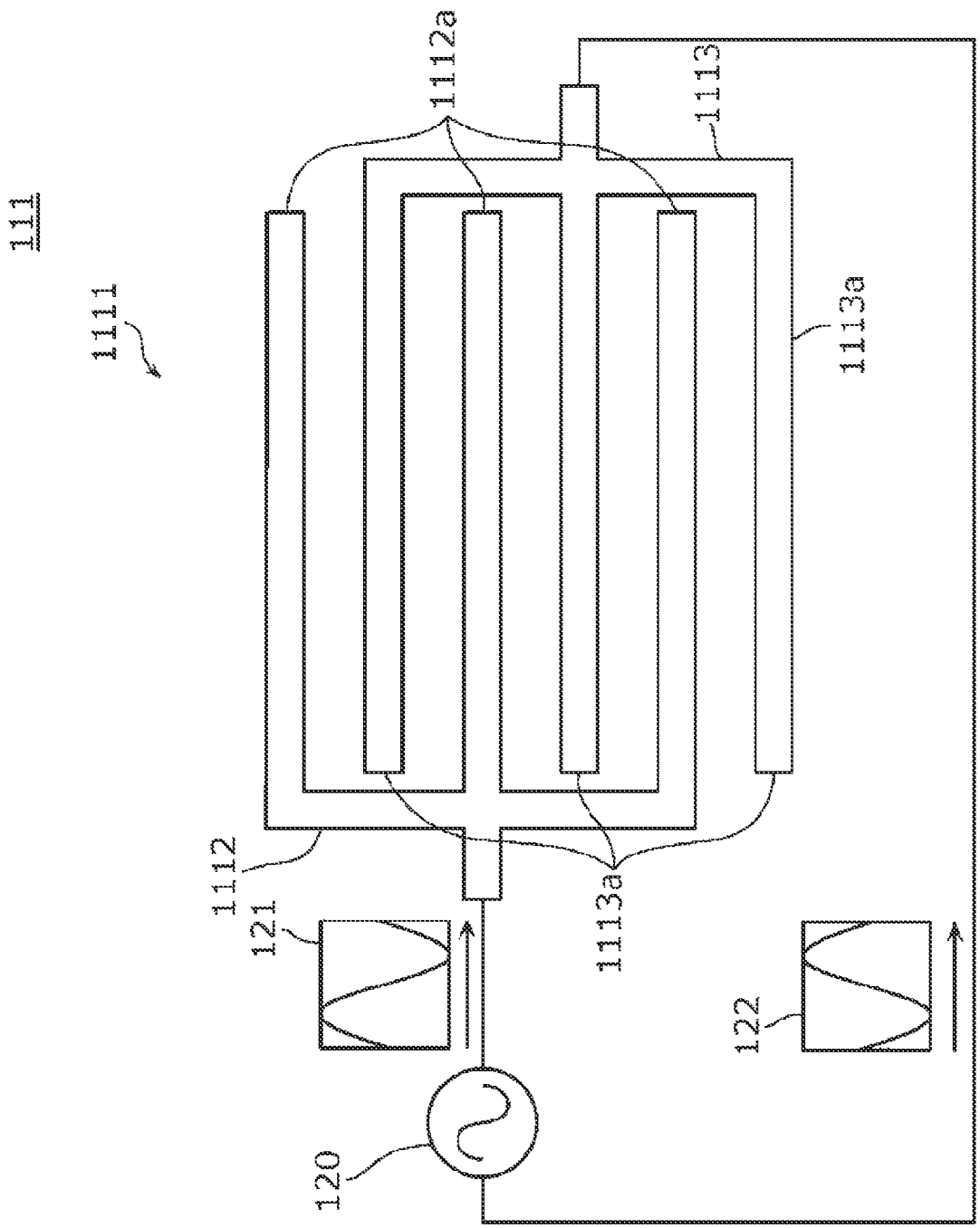
FIG. 2 is a diagram illustrating a configuration of a first electrode set on a first substrate in the embodiment.

A shape and an arrangement of the first electrode set 1111 on the first substrate 111 will be described next with reference to FIG. 2. FIG. 2 is a diagram illustrating a configuration of the first electrode set 1111 on the first substrate 111 in the embodiment. Specifically, FIG. 2 is an enlarged plan view of the first substrate 111 illustrated in FIG. 1.

As illustrated in FIG. 2, the first electrode set 1111 is constituted by interdigitated array electrodes formed on the first substrate 111 and includes a first electrode 1112 and a second electrode 1113. Each of the first electrode 1112 and the second electrode 1113 is electrically connected to the power source 120.

The first electrode 1112 has three first finger portions 1112a that extend in a first direction (a rightward direction in FIG. 2). Each of the first finger portions 1112a has a width of about 10 μm, for example. A gap between the adjacent first finger portions 1112a is about 20 μm, for example.

The second electrode 1113 has substantially the same shape and size as the first electrode 1112. The second electrode 1113 has three second finger portions 1113a that extend in a second direction (a leftward direction in FIG. 2) opposite to the first direction. One of the three first finger portion 1112a of the first electrode 1112 extends between the adjacent second finger portions 1113a.

A first AC voltage 121 and a second AC voltage 122 are respectively applied to the first electrode 1112 and the second electrode 1113 thus configured. The first AC voltage 121 and the second AC voltage 122 may have a phase difference of 180 degrees, for example.

Shape and Arrangement of Second Electrode Set 1131 on Second Substrate 113

Figure 3:
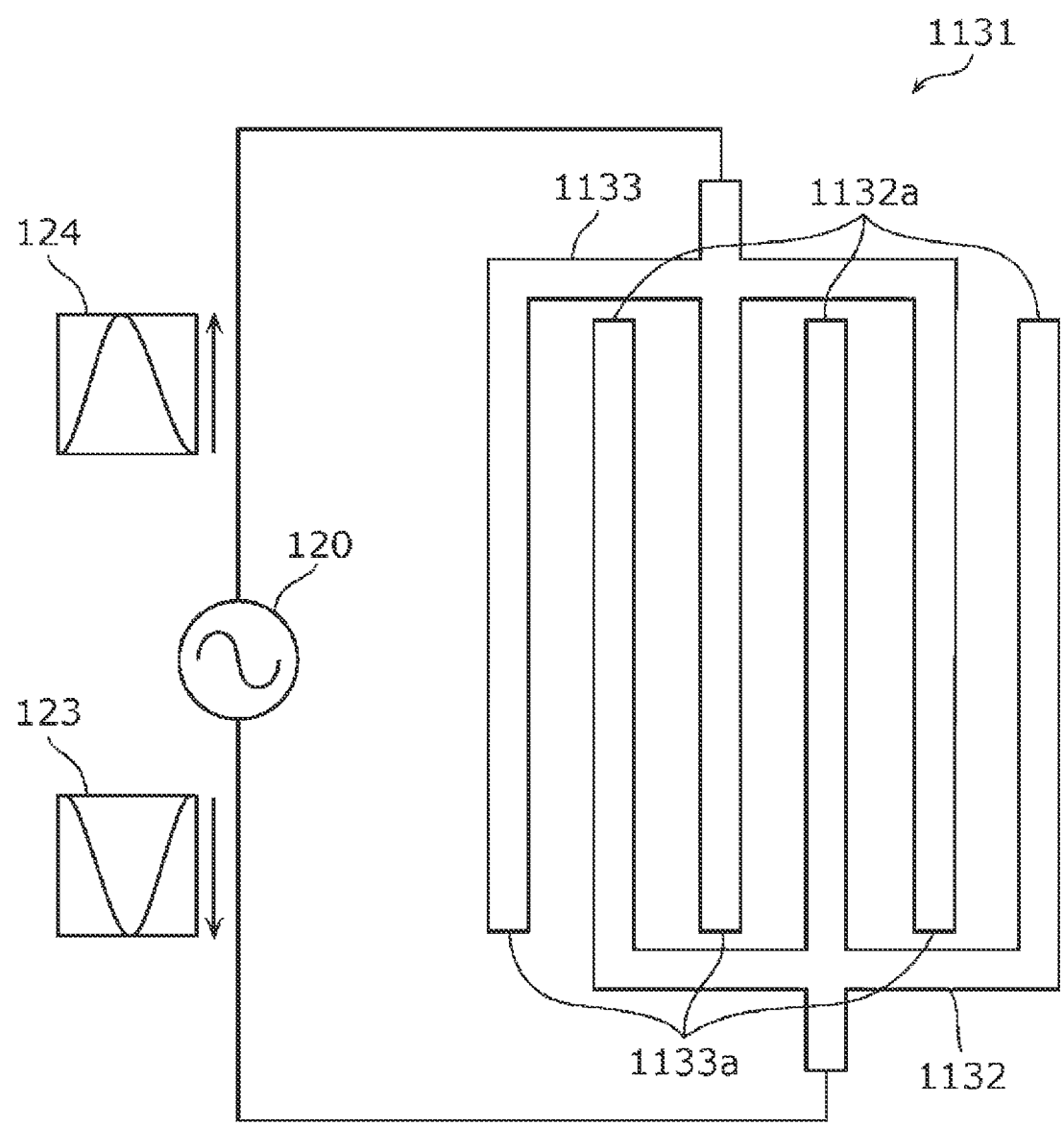
FIG. 3 is a diagram illustrating a configuration of a second electrode set on a second substrate in the embodiment.

A shape and an arrangement of the second electrode set 1131 on the second substrate 113 will be described next with reference to FIG. 3. FIG. 3 is a diagram illustrating a configuration of the second electrode set 1131 on the second substrate 113 in the embodiment.

As illustrated in FIG. 3, the second electrode set 1131 is constituted by interdigitated array electrodes formed on the second substrate 113 and includes a third electrode 1132 and a fourth electrode 1133. Each of the third electrode 1132 and the fourth electrode 1133 is electrically connected to the power source 120.

The third electrode 1132 has substantially the same shape and size as the first electrode 1112. The third electrode 1132 has three third finger portions 1132a that extend in a third direction (an upward direction in FIG. 2) perpendicular to the first direction or the second direction.

The fourth electrode 1133 has substantially the same shape and size as the first electrode 1112. The fourth electrode 1133 has three fourth finger portions 1133a that extend in a fourth direction (a downward direction in FIG. 2) opposite to the third direction. One of the three third finger portions 1132a of the third electrode 1132 extends between the adjacent fourth finger portions 1133a.

A third AC voltage 123 and a fourth AC voltage 124 are respectively applied to the third electrode 1132 and the fourth electrode 1133 thus configured. The third AC voltage 123 and the fourth AC voltage 124 may have a phase difference of 180 degrees, for example. In addition, the first AC voltage 121 and the third AC voltage 123, the third AC voltage 123 and the second AC voltage 122, the second AC voltage 122 and the fourth AC voltage 124, and the fourth AC voltage 124 and the first AC voltage 121 may have a phase difference of 90 degrees, for example. When the phase of the first AC voltage 121 is denoted by 0 degrees, the phases of the third AC voltage 123, the second AC voltage 122, and the fourth AC voltage 124 are respectively denoted by 90 degrees, 180 degrees, and 270 degrees. The applied first to fourth AC voltages have a frequency of about 100 to 2000 kHz, for example.

Positional Relationship Between First Electrode Set 1111 and Second Electrode Set 1131

Figure 4:
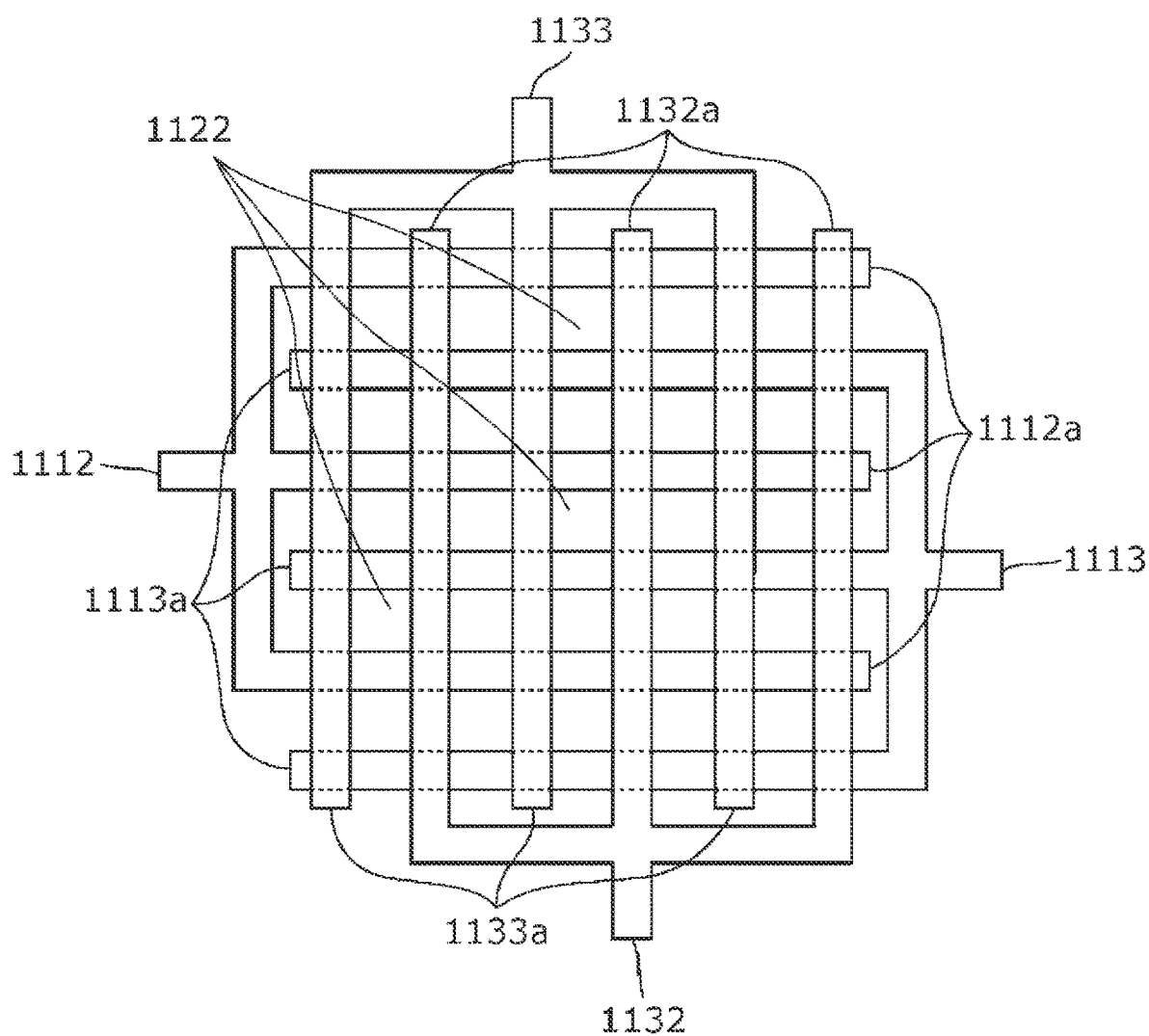
FIG. 4 is a projection diagram of the first electrode set and the second electrode set when the first substrate and the second substrate are viewed in plan in the embodiment.

A positional relationship between the first electrode set 1111 and the second electrode set 1131 will be described next. FIG. 4 is a projection diagram of the first electrode set 1111 and the second electrode set 1131 when the first substrate 111 and the second substrate 113 are viewed in plan in the embodiment.

The first substrate 111 and the second substrate 113 are disposed to face each other with the spacer 112 interposed therebetween. Thus, the first electrode set 1111 and the second electrode set 1131 partially overlap in plan view. Specifically, as illustrated in FIG. 4, the first finger portions 1112a and the second finger portions 1113a intersect with the third finger portions 1132a and the fourth finger portions 1133a at right angles at multiple positions in plan view. As a result, electric field regions 1122 each surrounded by the corresponding first finger portion 1112a, the corresponding second finger portion 1113a, the corresponding third finger portion 1132a, and the corresponding fourth finger portion 1133a are formed in the channel 1121 in plan view. The electric field regions 1122 each have a rectangular shape in FIG. 4. However, the shape is not limited to this. The case where there are three first finger portions 1112a, three second finger portions 1113a, three third finger portions 1132a, and three fourth finger portions 1133a has been described. However, the configuration is not limited to this, and it is sufficient that there are two or more first finger portions 1112a, two or more second finger portions 1113a, two or more third finger portions 1132a, and two or more fourth finger portions 1133a.

Detection Method Using Detection Device 100

Figure 5:
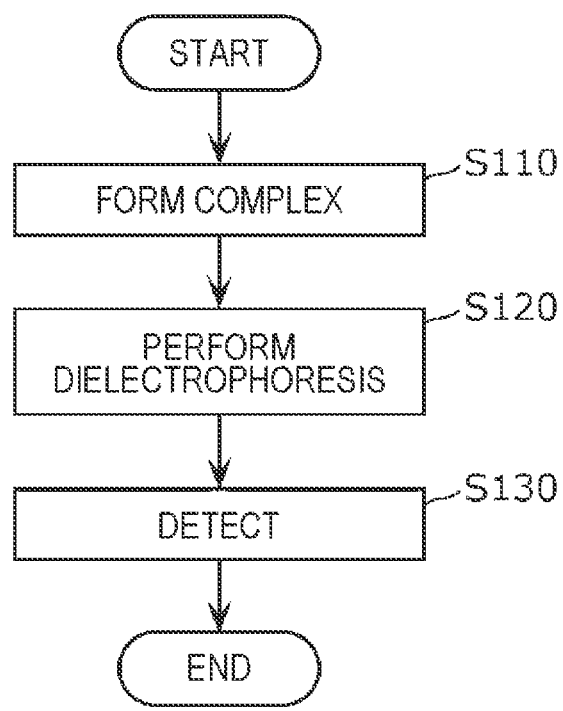
FIG. 5 is a flowchart of a detection method according to the embodiment.

A target substance detection method using the detection device 100 configured in the above-described manner will be described with reference to FIGS. 5 to 9. FIG. 5 is a flowchart of the detection method according to the embodiment.

Figure 6:
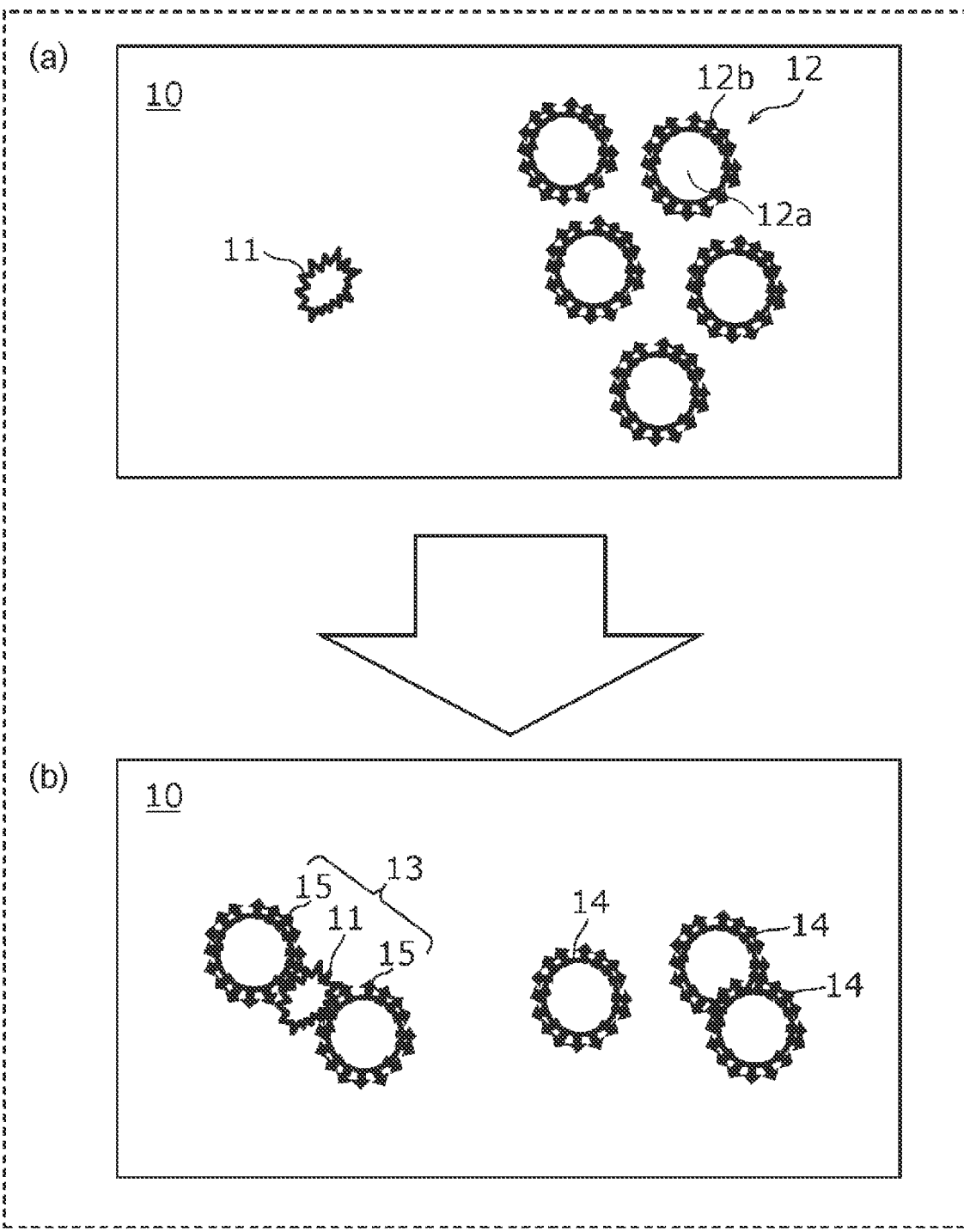
FIG. 6 is a diagram illustrating a process of forming a complex in the embodiment.

First, a complex is formed by causing a target substance and a dielectric particle modified with a substance that is capable of specifically binding to the target substance to bind to each other (S110). A process of forming a complex will now be described with reference to FIG. 6. FIG. 6 is a diagram illustrating the process of forming a complex 13 in the embodiment.

As illustrated in FIG. 6(a), antibody-modified dielectric particles 12 are mixed to the sample liquid 10 containing a target substance 11. Antibody-modified dielectric particles 12 are dielectric particles 12a each of which includes the fluorescent substance and is modified with antibodies 12b.

The antibodies 12b are an example of the substance having the property of specifically binding to the target substance 11. In this embodiment, VHH antibodies are adopted as the antibodies 12b. However, the antibodies 12b are not limited to this. The target substance 11, the dielectric particle 12a, and the antibody 12b have sizes of about 100 nm, about 300 nm, and about 5 nm, respectively.

The sample liquid 10 illustrated in FIG. 6(a) is left for a predetermined period at a predetermined temperature. Then, the target substance 11 and the antibody-modified dielectric particles 12 (hereinafter, referred to as bound particles 15) bind to each other by an antigen-antibody reaction, so that the complex 13 is formed as illustrated in FIG. 6(b). In this case, the complex 13 has a size of about 700 nm. The antibody-modified dielectric particles 12 that have not bound to the target substance 11 remain as unbound particles 14 in an isolated or aggregated state.

Note that the structure of the complex 13 illustrated in FIG. 6(b) is merely an example and is not limited to this. For example, the number of bound particles 15 may be three or more. For example, the number of bodies of the target substance 11 included in the complex 13 may be two or more.

The description returns to the flowchart of FIG. 5. The dielectrophoresis device 110 subjects the bound particles 15 and the unbound particles 14 to dielectrophoresis in the liquid (S120). Specifically, AC voltages are applied to the first electrode set 1111 and the second electrode set 1131. More specifically, the first AC voltage 121, the second AC voltage 122, the third AC voltage 123, and the fourth AC voltage 124 are respectively applied to the first electrode 1112, the second electrode 1113, the third electrode 1132, and the fourth electrode 1133. If the first AC voltage 121, the second AC voltage 122, the third AC voltage 123, and the fourth AC voltage 124 are set to have phase differences at this time, rotating electric fields are produced in the sample liquid 10.

Figure 7:
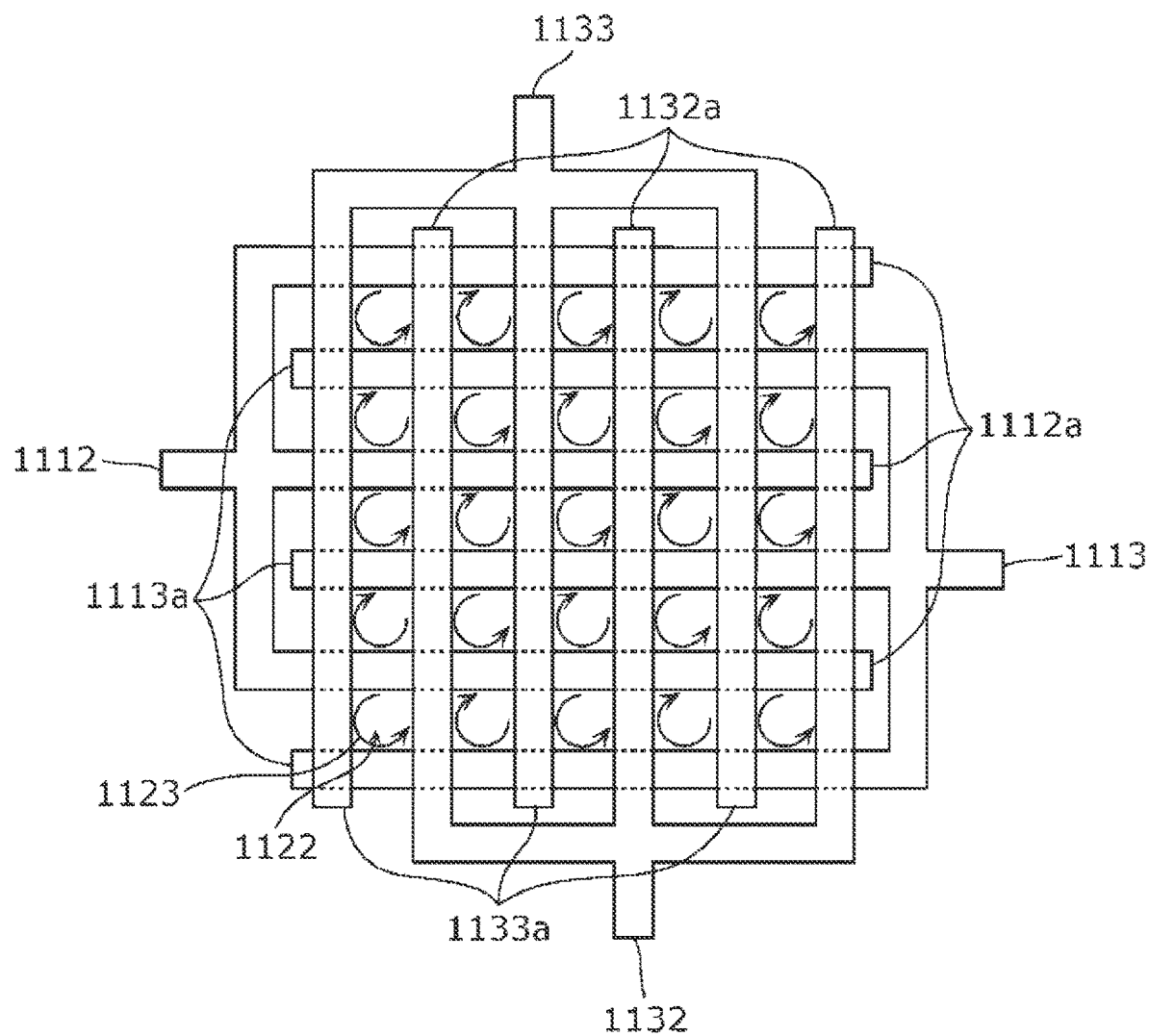
FIG. 7 is a diagram illustrating rotating electric fields in the embodiment.
Figure 8:
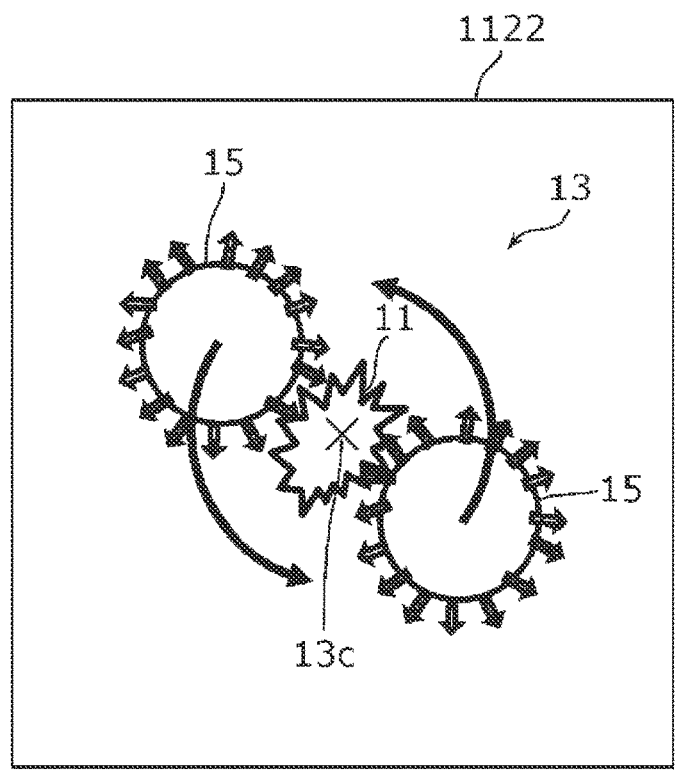
FIG. 8 is a diagram illustrating a motion of a complex in the embodiment.
Figure 9:
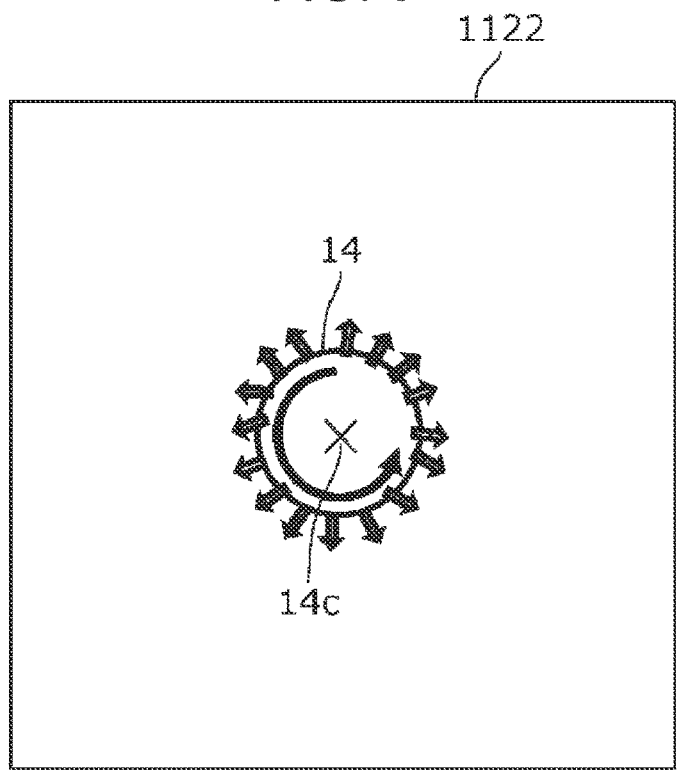
FIG. 9 is a diagram illustrating a motion of an unbound particle in the embodiment.

The rotating electric fields and dielectrophoresis will now be described with reference to FIGS. 7 to 9. FIG. 7 is a diagram illustrating rotating electric fields 1123 in the embodiment. FIG. 8 is a diagram illustrating a motion of the complex 13 in the embodiment. FIG. 9 is a diagram illustrating a motion of the unbound particle 14 in the embodiment.

As illustrated in FIG. 7, the clockwise or counterclockwise rotating electric field 1123 is produced in each of the electric field regions 1122 surrounded by the corresponding first finger portion 1112a, the corresponding second finger portion 1113a, the corresponding third finger portion 1132a, and the corresponding fourth finger portion 1133a in plan view. This rotating electric field 1123 causes the bound particles 15 and the unbound particles 14 in the electric field region 1122 to be subjected to dielectrophoresis, and the complex 13 and the unbound particles 14 move and rotate in the electric field region 1122. At this time, the unbound particles 14 in an aggregated state are split into the unbound particles 14 in an isolated state by dielectrophoresis.

In the case where two antibody-modified dielectric particles 12 bind to the target substance 11 to form the complex 13, the complex 13 in the electric field region 1122 moves toward the center of the electric field region 1122 and rotates around an axis passing through the center as illustrated in FIG. 8. At this time, a middle position 13c between the two antibody-modified dielectric particles 12 (that is, the two bound particles 15) constituting the complex 13 is located near the center of the electric field region 1122. Thus, the bound particles 15 each move to draw a circle. That is, the bound particles 15 each revolve around the axis apart from the bound particles 15.

In the case where one antibody-modified dielectric particle 12 binds to the target substance 11 to form the complex 13, a point shifted from the center position of the one antibody-modified dielectric particle 12 (that is, the one bound particle 15) constituting the complex 13 toward the center position of the target substance 11 is located near the center of the electric field region 1122. Thus, the one bound particle 15 rotates around an axis passing through this point. This case of one bound particle can be distinguished from the case of the unbound particle (described later) on the basis of a difference in rotating motion due to a difference in position of the rotation axis.

The unbound particle 14 in the electric field region 1122 moves toward the center of the electric field region 1122 and rotates around an axis passing through the center as illustrated in FIG. 9. At this time, a center position 14c of the unbound particle 14 is located near the center of the electric field region 1122. Thus, the unbound particle 14 turns on its axis. That is, the unbound particle 14 rotates around the axis passing through the center of the unbound particle 14. To confirm that the unbound particle 14 is turning on its axis, the fluorescent substance can be unevenly disposed at part of a surface of the dielectric particle or a portion serving as a maker can be provided at part of the surface of the dielectric particle.

The description returns to the flowchart of FIG. 5. Lastly, the detector 140 detects the target substance 11 included in the complex 13 based on a difference in motion between the bound particles 15 and the unbound particles 14 caused by dielectrophoresis (S130). Specifically, the image sensor 141 captures an image of the sample liquid 10 over time. The image processing circuit 142 processes the moving image obtained by image capturing to distinguish between the motion of the bound particles 15 and the motion of the unbound particles 14 in the sample liquid 10.

More specifically, for example, if a radius of a circular path of a light spot is greater than or equal to a threshold in the moving image, the image processing circuit 142 determines that the antibody-modified dielectric particle 12 corresponding to the light spot is the bound particle 15. On the other hand, if the radius of the circular path of the light spot is less than the threshold or if the light spot does not draw a circular path, the image processing circuit 142 determines that the antibody-modified dielectric particle 12 corresponding to the light spot is the unbound particle 14.

Advantageous Effects, Etc.

As described above, in the detection device 100 and the detection method according to this embodiment, the complex 13 is formed by causing the target substance 11 and the dielectric particles 12a modified with the antibodies 12b to bind each other; the bound particles 15 that are the antibody-modified dielectric particles 12 constituting the complex 13 and the unbound particles 14 that are the antibody-modified dielectric particles 12 not constituting the complex 13 are subjected to dielectrophoresis in the sample liquid 10; and the target substance 11 included in the complex 13 is detected based on a difference in motion between the bound particles 15 and the unbound particles 14 caused by the dielectrophoresis.

Thus, the unbound particles 14 that have aggregated by non-specific adsorption can be split into individual particles by dielectrophoresis, and false positives caused by non-specific adsorption can be reduced. The complex can be caused to move faster by dielectrophoresis than by magnetic forces. Thus, dielectrophoresis can make the detection time of the target substance 11 shorter than the detection time of the target substance 11 using magnetic forces.

In the detection device 100 and the detection method according to this embodiment, the rotating electric fields 1123 are produced in the sample liquid 10 to subject the bound particles 15 and the unbound particles 14 to the dielectrophoresis.

Thus, by producing the rotating electric fields in the sample liquid 10, a difference can be caused in motion between the bound particles 15 and the unbound particles 14.

In the detection device 100 and the detection method according to this embodiment, each of the bound particles 15 moves to draw a circular path by the dielectrophoresis, and each of the unbound particles 14 rotates around an axis passing through the center of the unbound particle 14 by the dielectrophoresis.

Thus, by distinguishing the circular path drawn by the bound particles 15, the target substance 11 included in the complex 13 can be detected. Consequently, target substance detection accuracy can be improved.

In the detection device 100 and the detection method according to this embodiment, the dielectric particles 12a each include a fluorescent substance, and in the detecting of the target substance 11, the sample liquid 10 is irradiated with the excitation light 131 and fluorescence emitted by the fluorescent substance included in each of the bound particles 15 and the unbound particles 14 is detected.

Thus, even when the dielectric particles 12a are small, the motion of the bound particles 15 and the motion of the unbound particles 14 can be easily distinguished between by detecting the fluorescence 132. Consequently, target substance detection accuracy can be improved.

In the detection device 100 and the detection method according to this embodiment, in the detecting of the target substance 11, an image of the sample liquid 10 is captured over time, and a moving image obtained by the image capturing is processed to distinguish between the motion of the bound particles 15 and the motion of the unbound particles 14 in the sample liquid 10.

Thus, the motion of the bound particles 15 and the motion of the unbound particles 14 can be easily distinguished between in the moving image. Consequently, target substance detection accuracy can be improved.

In the detection device 100 and the detection method according to this embodiment, the difference in motion between the bound particles 15 and the unbound particles 14 is distinguished based on a moving image obtained by using an imaging element.

MODIFICATIONS

The detection device and the detection method according to one or more aspects of the present disclosure have been described above based on the embodiment. However, the present disclosure is not limited to this embodiment. Various modifications conceivable by a person skilled in the art may be made on the embodiment without departing from the gist of the present disclosure, and such modifications may be within the scope of the one or more aspects of the present disclosure.

For example, in the embodiment described above, the rotating electric fields 1123 are used to subject the bound particles 15 and the unbound particles 14 to dielectrophoresis. However, the electric fields used are not limited to the rotating electric fields 1123. Any electric fields capable of causing dielectrophoresis that can create a difference in motion between the bound particles 15 and the unbound particles 14 may be used.

In the embodiment described above, interdigitated array electrodes are used to produce the rotating electric fields 1123. However, electrodes for producing the rotating electric fields 1123 are not limited to this type. For example, configurations such as the number of finger portions of each electrode and an arrangement of each electrode are not limited to the configurations illustrated in FIGS. 2 to 4.

In the embodiment described above, the first electrode set 1111 is formed on the first substrate 111 and the second electrode set 1131 is formed on the second substrate 113. However, the configuration is not limited to this. For example, both the first electrode set 1111 and the second electrode set 1131 may be formed on one of the first substrate 111 and the second substrate 113.

The detection device 100 can be used as a detection device for detecting a virus such as an influenza virus.

What is claimed is:

1. A detection method comprising:
   forming a complex by causing a target substance and a dielectric particle to bind to each other, the dielectric particle being modified with a substance having a property of specifically binding to the target substance;
   subjecting a bound particle and an unbound particle to dielectrophoresis in a liquid, the bound particle being the dielectric particle constituting the complex, the unbound particle being a dielectric particle not constituting the complex; and
   detecting the target substance included in the complex, based on a difference in motion between the bound particle and the unbound particle caused by the dielectrophoresis, wherein
   a rotating electric field is produced in the liquid to subject the bound particle and the unbound particle to the dielectrophoresis,
   the bound particle moves to draw a first circular path by the dielectrophoresis, a first radius of the first circular path being greater than or equal to a threshold,
   the unbound particle rotates around an axis passing through a center position of the unbound particle by the dielectrophoresis, a second radius of a second circular path on the basis of the rotation of the unbound particle being less than the threshold, and the difference in motion between the bound particle and the unbound particle caused by the dielectrophoresis is a difference between the first radius and the second radius.

2. The detection method according to claim 1, wherein the dielectric particle includes a fluorescent substance, and in the detecting of the target substance, the liquid is irradiated with excitation light and fluorescence emitted by the fluorescent substance included in each of the bound particle and the unbound particle is detected.

3. The detection method according to claim 1, wherein in the detecting of the target substance, an image of the liquid is captured over time, and a moving image obtained by the image capturing is processed to distinguish between the motion of the bound particle and the motion of the unbound particle in the liquid.

4. The detection method according to claim 1, wherein the difference in motion is distinguished based on a moving image obtained by using an imaging element.

5. A detection device comprising:

a dielectrophoresis device that subjects a bound particle and an unbound particle to dielectrophoresis in a liquid, the bound particle being a dielectric particle constituting a complex, the unbound particle being a dielectric particle not constituting the complex, the complex being a complex of a target substance that has bound to a dielectric particle modified with a substance having a property of specifically binding to the target substance; and a detector that detects the target substance included in the complex, based on a difference in motion between the bound particle and the unbound particle caused by the dielectrophoresis, wherein the dielectrophoresis device produces a rotating electric field in the liquid to subject the bound particle and the unbound particle to the dielectrophoresis, the bound particle moves to draw a first circular path by the dielectrophoresis, a first radius of the first circular path being greater than or equal to a threshold, the unbound particle rotates around an axis passing through a center position of the unbound particle by the dielectrophoresis, a second radius of a second circular path on the basis of the rotation of the unbound particle being less than the threshold, and the difference in motion between the bound particle and the unbound particle caused by the dielectrophoresis is a difference between the first radius and the second radius.

* * * * *